(12) United States Patent
Nelson et al.

(10) Patent No.: US 12,220,304 B2
(45) Date of Patent: Feb. 11, 2025

(54) EXPANDABLE ABSORBENT CORE AND METHOD OF MANUFACTURE

(71) Applicant: Curt G. Joa, Inc., Sheboygan Falls, WI (US)

(72) Inventors: Christopher J. Nelson, Plymouth, WI (US); Scott A. Roehrborn, Sheboygan, WI (US); Troy L. Bruckschen, Howards Grove, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 1245 days.

(21) Appl. No.: 16/596,843

(22) Filed: Oct. 9, 2019

(65) Prior Publication Data

US 2020/0121525 A1    Apr. 23, 2020

Related U.S. Application Data

(60) Provisional application No. 62/746,963, filed on Oct. 17, 2018.

(51) Int. Cl.
*A61F 13/537* (2006.01)
*A61F 13/15* (2006.01)
(Continued)

(52) U.S. Cl.
CPC .. *A61F 13/53708* (2013.01); *A61F 13/15739* (2013.01); *A61F 13/53409* (2013.01);
(Continued)

(58) Field of Classification Search
CPC .......... A61F 13/15; A61F 13/47; A61F 13/53; A61F 13/51; A61F 13/15203;
(Continued)

(56) References Cited

U.S. PATENT DOCUMENTS

| D28,672 S | 5/1898 | Takvorian |
| 1,702,530 A | 2/1929 | Williams |

(Continued)

FOREIGN PATENT DOCUMENTS

| EP | 3711731 A1 | 9/2020 |
| JP | 2005137648 A | 6/2005 |

(Continued)

OTHER PUBLICATIONS

International Search Report and Written Opinion for International Patent Application No. PCT/US23/63177, dated Aug. 28, 2023, 12 pages.

(Continued)

*Primary Examiner* — Michele Kidwell
(74) *Attorney, Agent, or Firm* — Klintworth & Rozenblat IP LLP

(57) ABSTRACT

An expandable absorbent structure comprises an expansion loop core configured to expand in response to absorption of a liquid and an expansion loop material structure surrounding the expansion loop core and having a trough therein, wherein the trough is formed from a first portion of the expansion loop material structure folded over a second portion of the expansion loop material structure at a first elbow of the expansion loop material structure. In response to an increase in size of the expansion loop core, the expansion loop core presses against the expansion loop material structure to cause a length of the trough to decrease.

13 Claims, 9 Drawing Sheets

(51) Int. Cl.
*A61F 13/53* (2006.01)
*A61F 13/534* (2006.01)
*A61F 13/551* (2006.01)
*A61F 13/56* (2006.01)

(52) U.S. Cl.
CPC ...... *A61F 13/5376* (2013.01); *A61F 13/5514* (2013.01); *A61F 13/5611* (2013.01); *A61F 2013/530481* (2013.01); *A61F 2013/530883* (2013.01); *A61F 2013/53765* (2013.01)

(58) Field of Classification Search
CPC .. A61F 13/5323; A61F 13/534; A61F 13/535; A61F 13/539; A61F 2013/530481; A61F 13/537; A61F 2013/53908; C08L 77/00; A01K 23/00; A47L 13/17
See application file for complete search history.

(56) References Cited

U.S. PATENT DOCUMENTS

| | | |
|---|---|---|
| 2,628,764 A | 2/1953 | Rubinstein et al. |
| 2,705,497 A | 4/1955 | Johnson et al. |
| 2,860,637 A | 11/1958 | Paul |
| 2,949,114 A | 8/1960 | De |
| 2,960,089 A | 11/1960 | Harwood et al. |
| 2,971,511 A | 2/1961 | Harwood |
| 2,992,644 A | 7/1961 | Plantinga et al. |
| 3,171,410 A | 3/1965 | Towle et al. |
| 3,256,881 A | 6/1966 | Stenvall |
| 3,329,145 A | 7/1967 | De |
| 3,494,362 A | 2/1970 | Burgeni |
| 4,201,332 A | 5/1980 | Wooten |
| 4,615,696 A | 10/1986 | Jackson et al. |
| 4,654,040 A | 3/1987 | Luceri |
| 4,675,013 A | 6/1987 | Ruffo |
| 5,037,418 A | 8/1991 | Kons et al. |
| 5,171,388 A | 12/1992 | Hoffman |
| 5,300,054 A | 4/1994 | Feist et al. |
| 5,304,160 A | 4/1994 | Igaue et al. |
| D347,893 S | 6/1994 | Gegelys et al. |
| 5,527,303 A | 6/1996 | Milby, Jr. et al. |
| 5,558,657 A | 9/1996 | Hammons et al. |
| 5,558,663 A | 9/1996 | Weinberger et al. |
| 5,584,829 A | 12/1996 | Lavash et al. |
| 5,591,297 A | 1/1997 | Ahr |
| 5,676,652 A | 10/1997 | Hunter et al. |
| D394,713 S | 5/1998 | Darcey et al. |
| 5,755,711 A | 5/1998 | Hammons et al. |
| 5,855,719 A | 1/1999 | Menard |
| 5,891,121 A | 4/1999 | Redwine et al. |
| 5,994,614 A | 11/1999 | Wada et al. |
| 6,068,620 A | 5/2000 | Chmielewski |
| 6,149,638 A | 11/2000 | Vogt et al. |
| 6,191,340 B1 * | 2/2001 | Carlucci ........... A61F 13/47227 604/385.04 |
| 6,277,104 B1 | 8/2001 | Lasko et al. |
| 6,316,688 B1 | 11/2001 | Hammons et al. |
| 6,773,421 B2 | 8/2004 | Bosselaar et al. |
| 6,838,591 B2 | 1/2005 | Waksmundzki et al. |
| 7,285,178 B2 | 10/2007 | Mischler et al. |
| D606,876 S | 12/2009 | Grullon |
| 8,377,025 B2 | 2/2013 | Nakajima et al. |
| 8,721,611 B2 | 5/2014 | Elfsberg et al. |
| 8,772,570 B2 | 7/2014 | Kawakami et al. |
| 8,961,487 B2 | 2/2015 | Tsang et al. |
| 9,084,698 B2 | 7/2015 | Ichikawa et al. |
| 9,095,479 B2 | 8/2015 | Glaug et al. |
| 9,180,058 B2 | 11/2015 | Ichihara et al. |
| 9,289,332 B2 | 3/2016 | Wade et al. |
| 9,358,162 B2 | 6/2016 | Kuwano et al. |
| 9,592,316 B2 | 3/2017 | Ichihara et al. |
| 9,814,634 B2 | 11/2017 | Schröder et al. |
| 9,980,856 B2 * | 5/2018 | Wilson .................. A61F 13/474 |
| 2001/0018578 A1 | 8/2001 | Imai et al. |
| 2001/0041879 A1 | 11/2001 | Karami et al. |
| 2001/0044610 A1 | 11/2001 | Kim et al. |
| 2002/0010511 A1 | 1/2002 | Michelson |
| 2002/0042600 A1 | 4/2002 | Datta et al. |
| 2002/0115971 A1 | 8/2002 | Holmes et al. |
| 2003/0055390 A1 | 3/2003 | Imai et al. |
| 2003/0144641 A1 | 7/2003 | Chen et al. |
| 2004/0186450 A1 | 9/2004 | Hermansson et al. |
| 2005/0147711 A1 | 7/2005 | Walter et al. |
| 2006/0065354 A1 | 3/2006 | Mischler et al. |
| 2006/0212012 A1 | 9/2006 | Carlos et al. |
| 2006/0266467 A1 | 11/2006 | Mlinar |
| 2010/0280475 A1 | 11/2010 | Kudo et al. |
| 2011/0251577 A1 | 10/2011 | Suzuki et al. |
| 2012/0197226 A1 | 8/2012 | Nakatani |
| 2012/0310195 A1 | 12/2012 | Toda et al. |
| 2012/0310201 A1 | 12/2012 | Oates |
| 2013/0002579 A1 | 1/2013 | Hatano |
| 2013/0066290 A1 | 3/2013 | Kawakami et al. |
| 2013/0240125 A1 | 9/2013 | Nelson et al. |
| 2014/0046286 A1 | 2/2014 | Homann et al. |
| 2014/0081230 A1 | 3/2014 | Litvay |
| 2014/0163500 A1 | 6/2014 | Roe et al. |
| 2015/0057632 A1 | 2/2015 | Luzader et al. |
| 2015/0080831 A1 | 3/2015 | Munakata et al. |
| 2015/0305949 A1 | 10/2015 | Glaug et al. |
| 2016/0045380 A1 | 2/2016 | Cree |
| 2016/0128875 A1 | 5/2016 | Ichikawa |
| 2016/0151213 A1 | 6/2016 | Bauduin et al. |
| 2016/0158073 A1 | 6/2016 | Wade et al. |
| 2016/0175169 A1 | 6/2016 | Bianchi et al. |
| 2016/0338884 A1 | 11/2016 | Quincy et al. |
| 2017/0055786 A1 | 3/2017 | Tyszka |
| 2017/0102306 A1 | 4/2017 | Dagher et al. |
| 2017/0172818 A1 * | 6/2017 | Suzuki ................ A61F 13/4758 |
| 2018/0021168 A1 | 1/2018 | Isaac et al. |
| 2018/0271720 A1 | 9/2018 | Tange et al. |
| 2018/0280207 A1 | 10/2018 | Harris et al. |
| 2019/0000697 A1 | 1/2019 | Sheehan et al. |
| 2019/0031422 A1 | 1/2019 | Lai et al. |
| 2019/0053956 A1 | 2/2019 | Nakamura et al. |
| 2020/0078229 A1 | 3/2020 | Van Ingelgem et al. |

FOREIGN PATENT DOCUMENTS

| | | |
|---|---|---|
| JP | 2011024887 A | 2/2011 |
| WO | 2013099557 A1 | 7/2013 |

OTHER PUBLICATIONS

International Search Report and Written Opinion for International Patent Application No. PCT/US23/63175, dated Jul. 6, 2023, 15 pages.

* cited by examiner

EXPANDABLE ABSORBENT CORE AND METHOD OF MANUFACTURE

CROSS-REFERENCE TO RELATED APPLICATIONS

The present invention is a non-provisional of and claims priority to U.S. Provisional Patent Application Ser. No. 62/746,963, filed Oct. 17, 2018, the disclosure of which is incorporated herein by reference in its entirety.

BACKGROUND OF THE INVENTION

Embodiments of the present invention relate to hygiene products and, more specifically, to absorbent core assemblies integrated within hygiene products for absorbing liquid materials.

Generally, hygiene products provide for an insert or garment application. In the case of hygiene products provided as inserts, the insert generally contains an insert first side, an insert second side, and a core assembly. The insert first side is generally in removable communication with the undergarment on which the insert is applied. The insert second side is generally a woven material for receiving fluid from the environment or from the user of the hygiene product. The core assembly is positioned between the insert first side and the insert second side and generally comprises one or more cores and material, woven or non-woven, surrounding the one or more cores. The core assembly may additionally include an acquisition distribution layer (ADL).

The insert is designed to transfer fluid from the environment (e.g., user of the hygiene product) to the insert second side. The fluid transfers through the insert second side and into the core assembly. When entering the core assembly, the fluid transfers through the material surrounding the one or more cores and into the cores. The acquisition of fluid by the one or more cores results in the one or more cores increasing in size. It is observed that in the prior art the material surrounding the one or more is in fixed communication with the insert, wherein the insert forms a cavity for the one or more cores. However, in the prior art, the communication of the material to the insert provides for limited expansion of the material. As a result, the limited expansion of the material allows for limited expansion of the one or more cores. Therefore, the limited expansion of the one or more cores due to mechanisms including gel blocking, capillary action, and/or ionic attraction impedes the absorption efficiency of the one or more cores.

Accordingly, there is a need for an improved apparatus that allows greater expansion of the one or more cores to increase their absorption efficiency.

BRIEF STATEMENT OF THE INVENTION

Embodiments of the present invention are directed to the expansion of absorbent cores in hygiene products for undergarments. More specifically, embodiments of the present invention are directed to expansion loops providing for expansion capability of absorbent cores.

In accordance with one aspect of the invention, an expandable absorbent structure comprises an expansion loop core configured to expand in response to absorption of a liquid and an expansion loop material structure surrounding the expansion loop core and having a trough therein, wherein the trough is formed from a first portion of the expansion loop material structure folded over a second portion of the expansion loop material structure at a first elbow of the expansion loop material structure. In response to an increase in size of the expansion loop core, the expansion loop core presses against the expansion loop material structure to cause a length of the trough to decrease.

In accordance with another aspect of the invention, an absorbent product comprises a first core and an expansion loop positioned adjacently to the first core. The expansion loop comprises a second core configured to expand in response to absorption of a liquid and a loop material surrounding the second core. The loop material comprises a first portion, a second portion overlapping the first portion, and a first elbow joining the first portion to the second portion. The first portion, the second portion, and the first elbow form a trough. The first core and the second core expand in response to liquid absorption. In response to expansion of the second core, the second core presses against the loop material to reduce a length of the trough.

In accordance with another aspect of the invention, a method of making an expandable absorbent structure comprises positioning a liquid absorption core adjacently to a liquid permeable material and folding a first leg of the liquid permeable material about a first end of the liquid absorption core to create a trough in the first leg. The trough is formed by a first portion of the first leg, a second portion of the first leg overlapping the first portion, and an elbow of the first leg joining the first portion to the second portion. The method also comprises folding a second leg of the liquid permeable material about a second end of the liquid absorption core, the second end of the liquid absorption core opposite the first end of the liquid absorption core. The method also comprises bonding the first leg to the second leg.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the present invention provide for an apparatus and method for allowing the expansion of a liquid absorption core within a containing material to increase the size of the liquid absorption core without damaging or rupturing the containing material. The length of the containing material surrounding the liquid absorption core includes an amount of folded material that allows the containing material to unfold due to expansion of the liquid absorption core while enclosing the liquid absorption core in a close-fitting manner. While the absorbent cores are described herein as being integrated within hygiene products, it is contemplated that the absorbent cores may be utilized in other applications, including other types of absorbent sanitary products, medical products (e.g., wound care pads), and absorbent pads for use in the food packaging or automotive industries, and, on a larger scale, absorbent pads for use in environmental and industrial applications (e.g., oil or chemical spill cleanup).

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
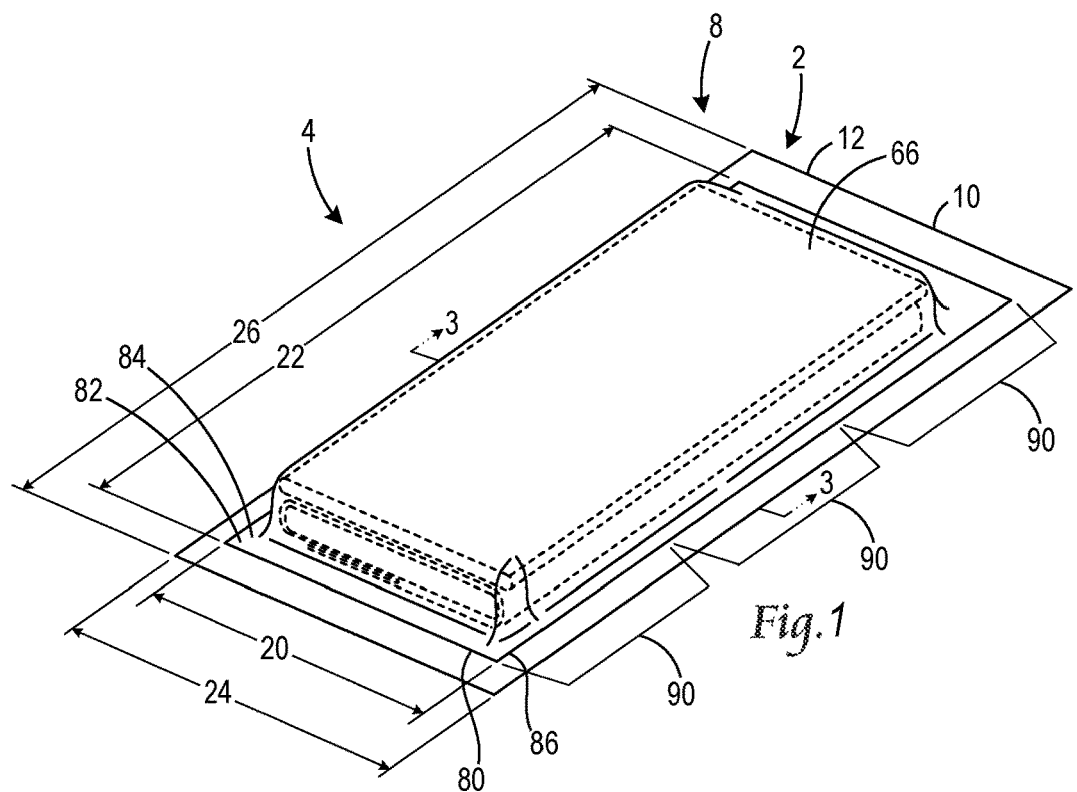
FIG. 1 is a perspective view of a hygiene product containing an expansion loop in communication with a case assembly according to a first embodiment of the invention.
Figure 1A:
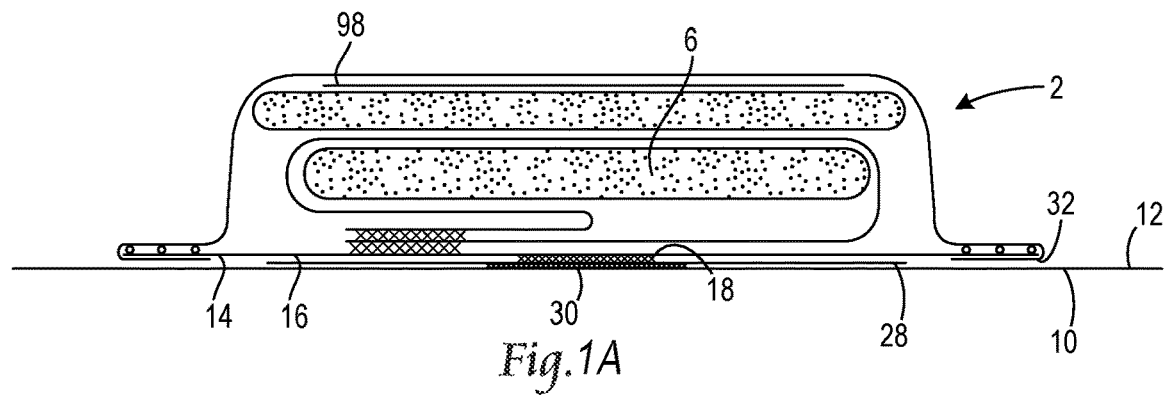
FIG. 1A is a cross-section of the hygiene product of FIG. 1.

Referring to FIGS. 1 and 1A, a hygiene product 2 that has a planar orientation 4 and includes an expansion loop material structure (referred to hereafter as expansion loop 6), which is illustrated inside a case assembly 8. It is understood that the hygiene product 2 may include any of the expansion loop embodiments disclosed herein. The case assembly 8 comprises a temporary backing 10. As further illustrated in FIG. 1A, the temporary backing 10 has a side 12 removably coupled with a reverse face side 14 of a sheet 16, typically of a poly film, of the hygiene product 2 via an adhesive film 18 attached to the reverse face side 14.

As illustrated in FIG. 1, the hygiene product 2 has a hygiene product width 20 and a hygiene product length 22 that are shorter than the respective width 24 and length 26 of the temporary backing 10 to ensure that the adhesive film 18 is protected from adhering to unwanted objects until the hygiene product 2 is ready for use. However, the temporary backing width 24 and length 26 may be the same size or may be shorter than the hygiene product width 20 and length 22 as long as the adhesive film 18 remains protected until use. A paper membrane 28 having a removable bond with the adhesive film 18 may be positioned between the poly sheet 16 and the temporary backing 10 to limit the amount of direct attachment of the temporary backing 10 to the adhesive film 18. The poly sheet 16 and the temporary backing 10 may be coupled together via a stronger adhesive bond 30 than the adhesive film 18 so that removal of the temporary backing 10 removes the paper membrane 28 from the adhesive film 18 at the same time. A first side 32 of the hygiene product 2 is exposed upon removal of the temporary backing 10 for placement on an undergarment (not illustrated in the FIGS.) to affix the hygiene product 2 to the undergarment during use.

Figure 1B:
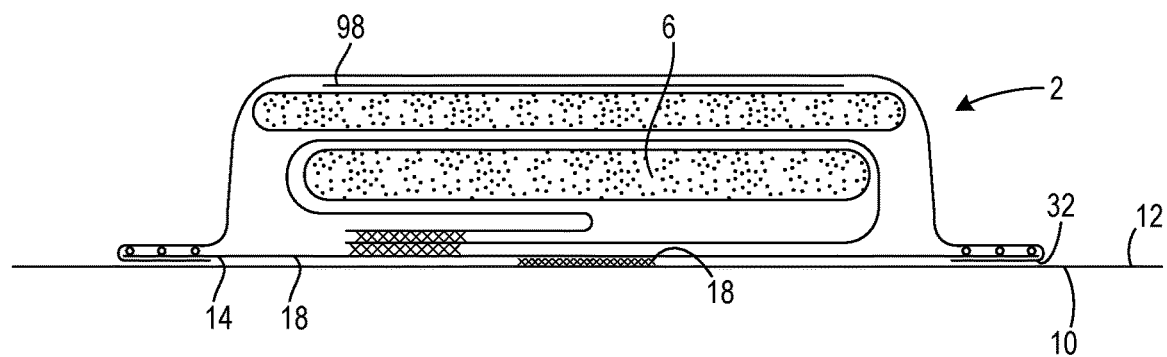
FIG. 1B is a cross-section of the hygiene product of FIG. 1 wherein a paper membrane is absent.

FIG. 1B illustrates the hygiene product 2 of FIG. 1 according to an alternative embodiment that does not include the paper membrane 28.

Figure 2:
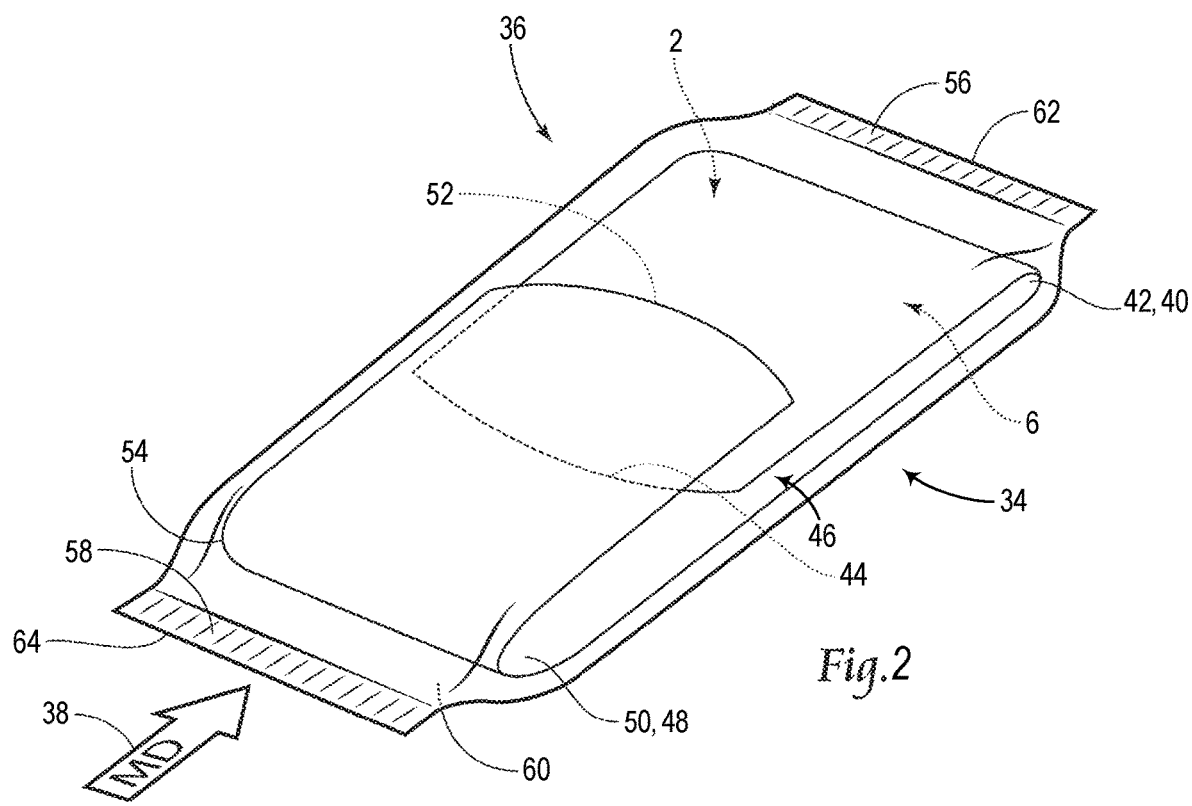
FIG. 2 is a perspective view of a hygiene product containing an expansion loop in communication with a case assembly according to an embodiment of the invention.

Referring to FIG. 2, the hygiene product 2 in a tri-fold configuration 34 is illustrated in a package assembly 36, which provides for the hygiene product 2 to be oriented such that the hygiene product length 22 is positioned in a machine direction 38. The hygiene product 2 has a first fold 40 made at a first location 42 along the hygiene product length 22 such that the first fold 40 is substantially orthogonal to the hygiene product length 22. The first fold 40 is oriented such that a first end 44 of the hygiene product 2 is in close proximity to a medial section 46 of the hygiene product 2. A second fold 48 is made at a second location 50 along the hygiene product length 22 such that the second fold 48 is in close proximity to the hygiene product second end 50. The second fold 48 is substantially orthogonal to the hygiene product length 22 and oriented such that a second end 52 overlaps the first end 44 or vice versa.

The package assembly 36 includes an outer package 54 having a first seal 56, a second seal 58 and a package cavity 60. The first seal 56 provides for a first package end 62, and the second seal 58 provides for a second package end 64. The hygiene product 2 is positionable in the package cavity 60 in a first position as shown where the first fold 40 and the second fold 48 are respectively in close proximity to first package end 62 and the second package end 64. The first seal 56 and the second seal 58 preferably comprise an ultrasonic seal. Alternatively, the first and second seals 56, 58 may comprise one or more of the ultrasonic seal, a chemical seal, and a mechanical seal. The second embodiment package 54 may be preferably separated from the second embodiment package cavity 60 via either package end 62, 64.

Figure 3:
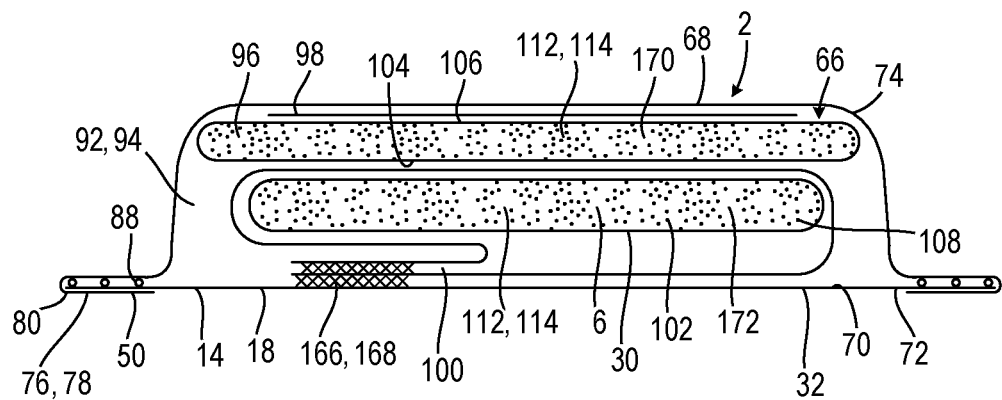
FIG. 3 is a cross-section of the hygiene product of FIG. 1 according to an embodiment of the invention.

As illustrated in FIGS. 1 and 3, the hygiene product 2 includes a core assembly 66 and has a second side 68. The first side 32 comprises a first side cavity face 70 and a reverse face side 14 opposite the first side cavity face 70. The first side 32 comprises an impermeable layer 72. The second side 68 comprises a woven layer 74. The first side 32 and the second side 68 are coupled together by, preferably, ultrasonic bonding 76 and/or adhesive bonding 78 to form a perimeter 80. In the illustrated embodiment, an edge 82 of the woven layer 74 at a first edge 84 and a second edge 86 of the perimeter 80 include an elastic strand 88 to provide one or more regions of elasticity 90 along the hygiene product length 22. The elastic strand 88 may be omitted in alternative embodiments.

As illustrated in FIG. 3, a cavity 92 formed between the first side 32 and the second side 68 has a space 94 for the core assembly 66. The core assembly 66 comprises the expansion loop 6, a second core 96, and an acquisition distribution layer (ADL) 98. An expansion loop arm 100 of the expansion loop 6 is positioned adjacently to the first side cavity face 70. The expansion loop arm 100 is preferably coupled to the first side cavity face 70. A body or core 102 of the expansion loop 6 is positioned adjacently to a first side 104 of the second core 96 to receive liquid not absorbed by the second core 96. A second side 106 of the second core 96, opposite the first side 104, is preferably in communication with the ADL 98 to receive liquid therefrom. The ADL 98 is positioned adjacently to the second side 68 to receive liquid from the environment outside the hygiene product 2. The body 102 preferably includes a liquid absorbent material 108 as a fill that expands upon absorption of a liquid. A perimeter 110 of the body 102 thus increases as the liquid absorbent material 108 absorbs the liquid and expands. The liquid absorbent material 108 may include a fibrous material 112 and/or a super absorbent polymer (SAP) 114 for absorbing the liquid.

In an alternate embodiment, the expansion loop 6 and second core 96 may be positioned in a flipped orientation with the expansion loop 6 stacked atop the second core 96. In yet other embodiments, second core 96 may be omitted entirely.

Figure 4:
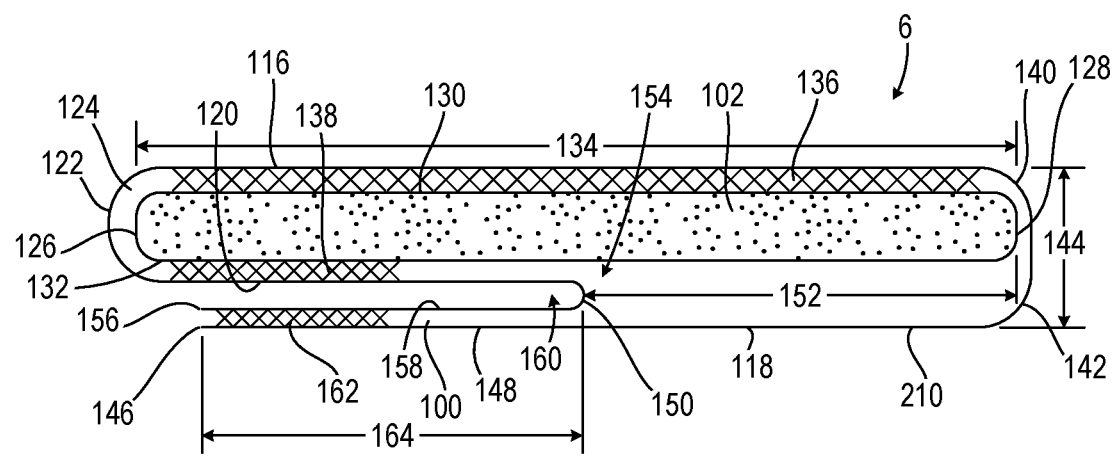
FIG. 4 is a cross-section of the expansion loop of FIG. 1 according to an embodiment of the invention.

Referring to FIGS. 1, 3 and 4, the expansion loop 6 includes an expansion loop material 116 surrounding the core 102. The expansion loop material 116 is a non-stretchable liquid-permeable material. The expansion loop material 116 includes a continuous sheet of material having a first leg 118 and a second leg 120 joined by a first elbow 122, which provide for an expansion loop cavity 124 having the core 102 positioned therein. The core 102 has a first side 126 and second side 128 opposite the first side 126. The first leg 118 and second leg 120 wrap around the core 102 from a first face 130 of the core 102 to a second face 132 of the core 102.

A core width 134 extends between the first side 126 and the second side 128. A first adhesive 136 secures the core 102 to the expansion loop material 116 and, in the embodiment shown in FIG. 4, extends a majority of the core width 134 between the first side 126 and the second side 128. Alternatively, selective applications of the first adhesive 136 at multiple locations within the core width 134 are also contemplated. In addition, a second adhesive 138 may be applied to secure a portion of the second face 132 of the core 102 to the second leg 120.

The first leg 118 has a second elbow 140, a third elbow 142, and a second side length 144 between the second and third elbows 140, 142. Following the third elbow 142, the first leg 118 has a first leg end 146 in close proximity to the first side 126, wherein a section 148 of the first leg 118 between the third elbow 142 and the first leg end 146 is positioned near the second face 132.

The second leg 120 has a fourth elbow 150 positioned at a distance 152 from the second side 128. In the illustrated embodiment, the fourth elbow 150 is positioned in a middle section 154 of the core width 134. Alternatively, the distance 152 may extend more or less than the middle section 154 such that, for example, the distance 152 may be in closer proximity to one of the first or second sides 126, 128 than to the middle section 154. Following the fourth elbow 150, the second leg 120 has a second leg end 156 in close proximity to the first side 126, where a second leg section 158 of the second leg 120 between the fourth elbow 150 and the second leg end 156 is positioned between the section 148 of the first leg 118 and the second face 132. The doubling-back of the second leg 120 at the fourth elbow 150 provides for a trough 160 having parallel or substantially parallel sides separated by a trough base (e.g., fourth elbow 150).

The first leg end 146 is in close proximity to the second leg end 156, which have a leg end adhesive 162 that provides for fixed communication between the first leg end 146 and the second leg end 156. The expansion loop arm 100 includes the first leg end 146 and the second leg end 156 and has an expansion loop arm length 164 between the fourth elbow 150 and the first and second leg ends 146, 156. The expansion loop arm 100 is preferably coupled to the first side cavity face 70. In one embodiment, a second adhesive 166 couples the first leg end 146 to the first side cavity face 70. Alternatively or in addition thereto, the expansion loop arm 100 may be coupled to the first side cavity face 70 via an ultrasonic bond 168. However, it is also contemplated that the expansion loop arm 100 is not coupled to the first side cavity face 70 in yet other embodiments.

The amount of leg end adhesive 162 extending from first leg end 146 toward fourth elbow 150 influences the amount of travel of the fourth elbow 150 during expansion of the core 102. In general, travel of the fourth elbow 150 or other folded-over section of the second leg section 158 toward the left as illustrated in FIG. 4 is limited by the edge of the leg end adhesive 162 closest to the fourth elbow 150. Once the edge of the leg end adhesive 162 is reached, further expansion of the expansion loop arm 100 is substantially prevented without incurring damage to the bond 162.

The length and width of the core 102 are less than the length and width of the second core 96 in one embodiment. Alternatively, the core 102 may be similarly sized with the second core 96 or may extend beyond the length and width of the second core 96. A thickness 170 of the second core 96 can be less than a thickness 172 of the core 102 as illustrated. Alternatively, the thickness 170 may be greater than or may be equal to the thickness 172.

Figure 5A:
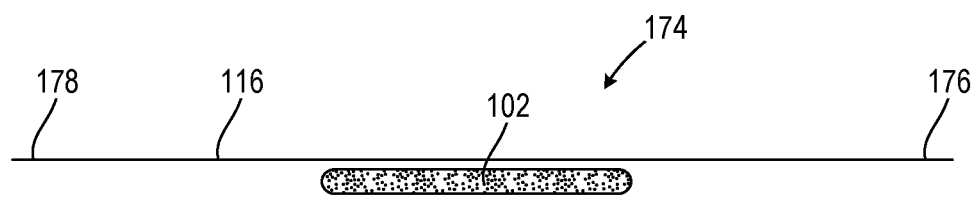
FIGS. 5A-D illustrate a method of manufacturing the expansion loop of FIG. 1 according to an embodiment of the invention.
Figure 5B:
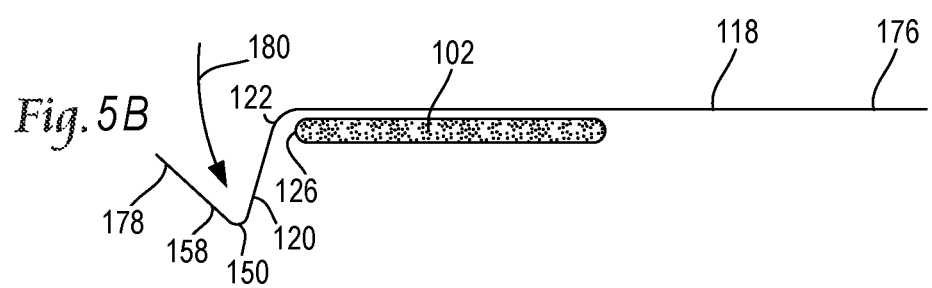
Figure 5C:
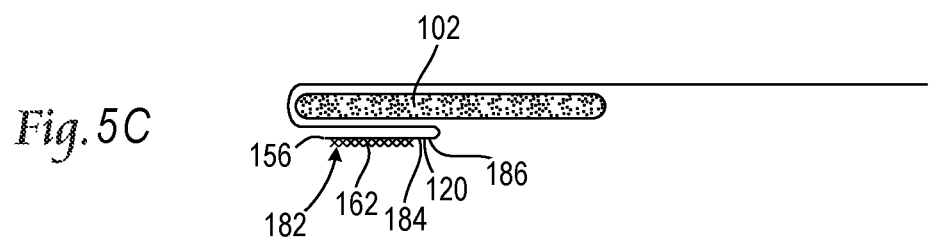
Figure 5D:
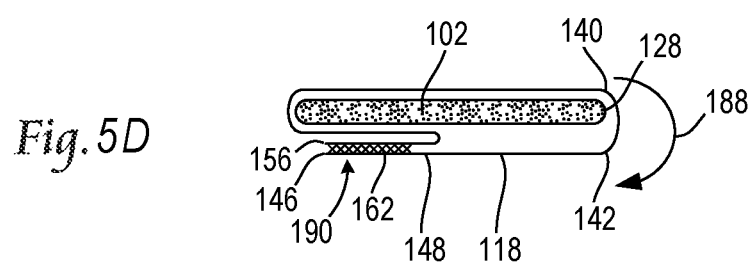

Referring to FIGS. 5A-5D, a method of manufacturing the expansion loop 6 is described as illustrated by cross-sectional views of the respective FIGS. As illustrated in FIG. 5A, the core 102 is positioned (step 174) in close proximity to the expansion loop material 116 having a first side 176 and a second side 178. Folding (step 180) the second side 178 about the expansion loop core first side 126 creates the first elbow 122, the fourth elbow 150, the second leg 120, and the second leg section 158. As illustrated, the fourth elbow 150 is positioned such that the distance 152 is substantially midway between the first and second sides 126, 128 of the core 102. Alternatively, the distance 152 may be closer in proximity to the first side 126 or to the second side 128. The leg end adhesive 162 is applied (step 182) to a leg face 184 of the second leg 120 close to the second leg end 156, wherein the leg face 184 is oriented 186 away from the core 102. Rotating (step 188) the first leg 118 about the expansion loop core second side 128 creates the second elbow 140 and third elbow 142 and provides for the section 148 of the first leg 118 to be positioned adjacently to the second leg 120. The first leg 118 and the second leg 120 are bonded (step 190) such that the first leg end 146 and the second leg end 156 are in close proximity.

Figure 6A:
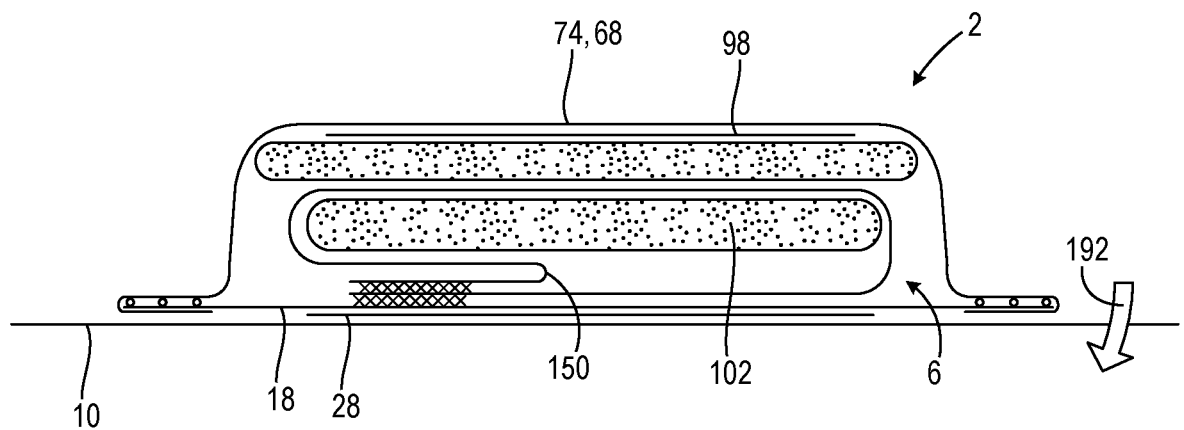
FIGS. 6A-D illustrate operation of the expansion loop of FIG. 1 according to an embodiment of the invention.
Figure 6B:
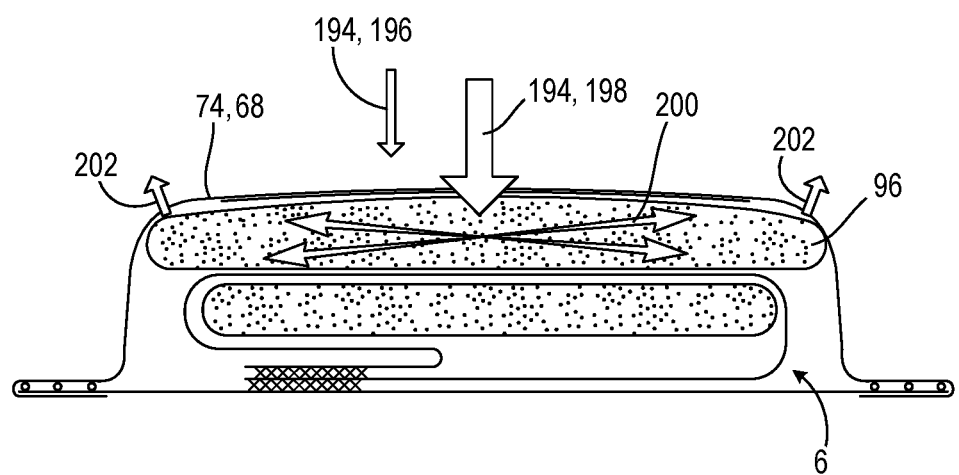

Referring to FIGS. 6A-6D, a method of operation of the expansion loop 6 is described. As illustrated in FIG. 6A, removal (step 192) of the temporary backing 10 allows the hygiene product 2 to be subsequently placed on an undergarment (not illustrated in the FIGS.) where the adhesive film 18 non-permanently attaches the hygiene product 2 to the undergarment. As illustrated in FIG. 6B, when a liquid is applied (step 194) to the hygiene product 2, the liquid enters (step 196) the second side 68 and proceeds to the ADL 98 (if provided), which distributes the liquid as known in the art. The liquid subsequently enters (step 198) the second core 96, which experiences expansion (step 200), causing the second core 96 to press (step 202) against the second side 68 of the hygiene product 2.

Figure 6C:
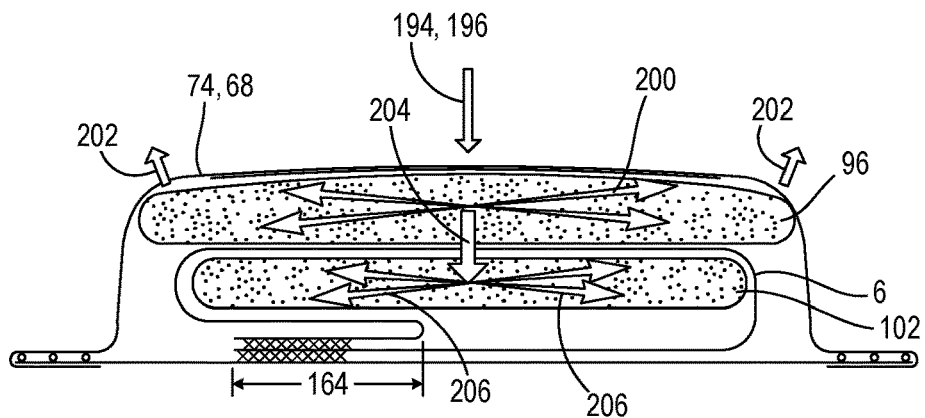

As illustrated in FIG. 6C, the liquid not absorbed by the second core 96 enters (step 204) the expansion loop 6 and core 102, which experiences expansion (step 206).

Figure 6D:
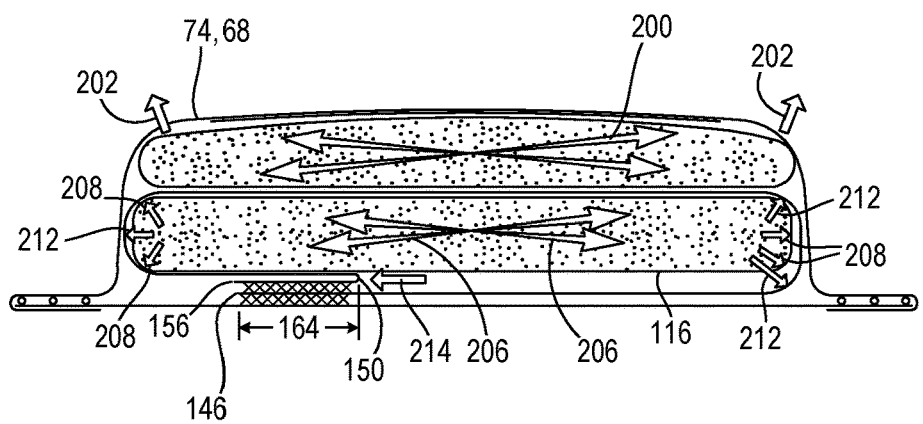

As illustrated in FIG. 6D, the core expansion 206 causes the core 102 to press (step 208) against the expansion loop material 116 surrounding the core 102. In one example, the expansion loop material 116 is not significantly elastic and, therefore, does not significantly stretch. Thus, a perimeter 210 of the expansion loop material 116 between the first leg end 146 and the second leg end 156 is substantially fixed. Therefore, the press 208 of the core 102 due to its expansion presses (step 212) against the expansion loop material 116 and causes the fourth elbow 150 to travel (step 214) toward the first and second leg ends 146, 156. The travel 214 and the press 208 reduce the expansion loop arm length 164.

Figure 7A:
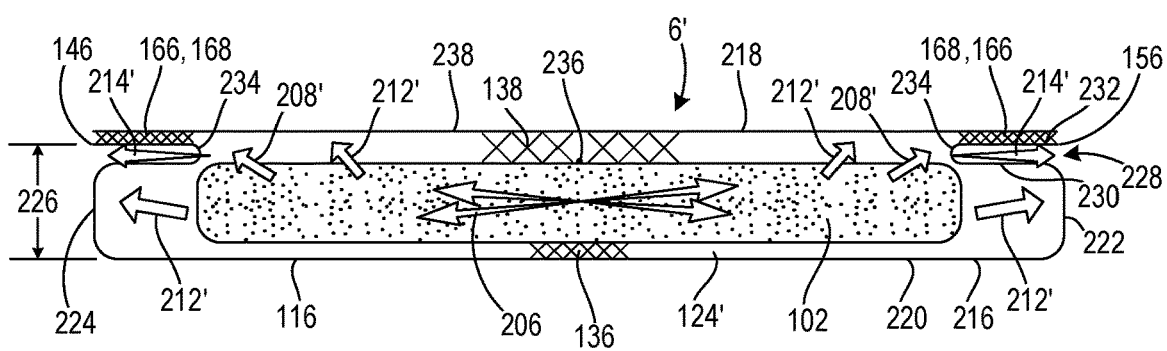
FIG. 7A is a cross-section of an expansion loop and operation thereof according to another embodiment of the invention.

Referring to FIG. 7A, an expansion loop 6' according to another embodiment is described. It is to be understood that references to a particular item or feature described hereafter provide that the item/feature in question may be singular or multiple in number. The expansion loop material 116 of the expansion loop 6' is wrapped around the core 102 by a pair of material sheets 216, 218 bonded together such that the wrapping by the expansion loop material 116 creates an expansion loop cavity 124'.

The expansion loop material 116 includes an expansion loop first side 220, an expansion loop first side wall 222 formed in the first material sheet 216, and an expansion loop second side wall 224 formed in the first material sheet 216. The expansion loop first side wall 222 extends from the expansion loop first side 220, and the expansion loop second side wall 224 extends from the expansion loop first side 220 similarly to the expansion loop first side wall 222 such that the core 102 resides between the expansion loop first side wall 222 and the expansion loop second side wall 224. Along the respective side wall lengths 226 of the expansion loop first side wall 222 and the expansion second side wall 224, each side wall 222, 224 has a respective a trough 228 formed therein. The trough 228 of each side wall 222, 224 has a trough first side 230 parallel to and corresponding with a trough second side 232. The trough first side 230 and the trough second side 232 are separated by a trough base or elbow 234. The trough base 234 of each trough 228 of each side wall 222, 224 extends toward a core central position 236.

An expansion loop second side 238, formed by the second material sheet 218, is bonded to the first material sheet 216 such that the expansion loop second side 238 is substantially parallel to the expansion loop first side 220. The expansion loop second side 238 is bonded through adhesive 166 or ultrasonic bonding 168 or another method of bonding to the trough second side 232.

As further illustrated in FIG. 7A, a method of operation of the expansion loop 6' is described. The core 102 experiences an expansion 206, causing the core 102 to press 208' against the expansion loop material 116 surrounding the core 102. The press 208' of the core 102 causes the respective trough base 234 of each side wall 222, 224 to travel 214' toward the respective side wall 222, 224.

Figure 7B:
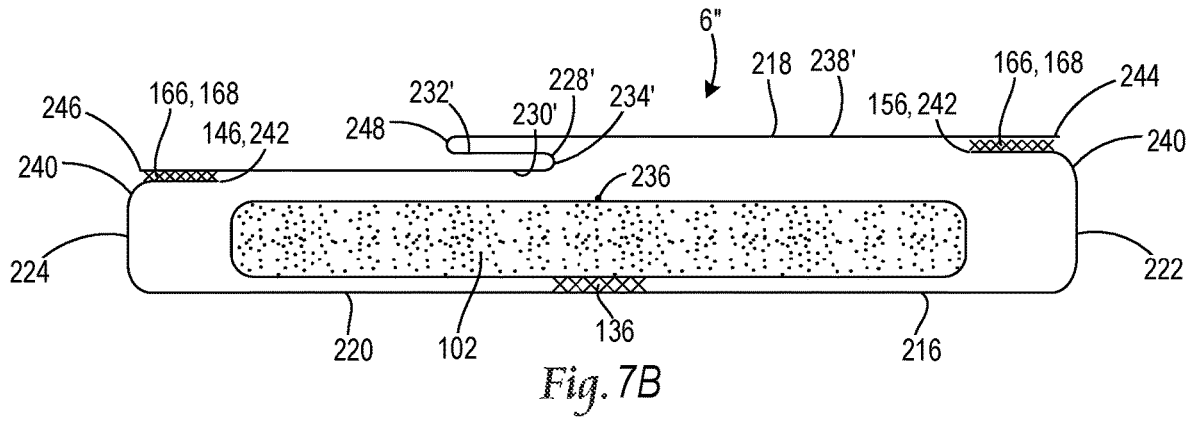
FIG. 7B is a cross-section of an expansion loop according to another embodiment of the invention.

FIG. 7B is a cross-section of an expansion loop 6" according to another embodiment of the invention. Each side wall 222, 224 includes a bend 240 in close proximity to the first and second leg ends 146, 156 at side wall ends 242 corresponding to the first and second leg ends 146, 156. The bend 240 extends the respective side wall 222, 224 in the direction toward the core central position 236. A second side 238' of the expansion loop 6" is coupled with each side wall (222, 224) at respective first and second leg ends 244, 246. The second side 238' is bonded through adhesive 166 or ultrasonic bonding 168 or another method of bonding to each side wall 222, 224. The second side 238' includes trough 228' having a first trough side 230', a trough second side 232', and a trough base 234'. Since the trough elbow 234' causes the trough second side 232' to extend away from the first leg end 244, a second elbow 248 is introduced to fold the material sheet 218 back toward the first leg end 244.

Figure 7C:
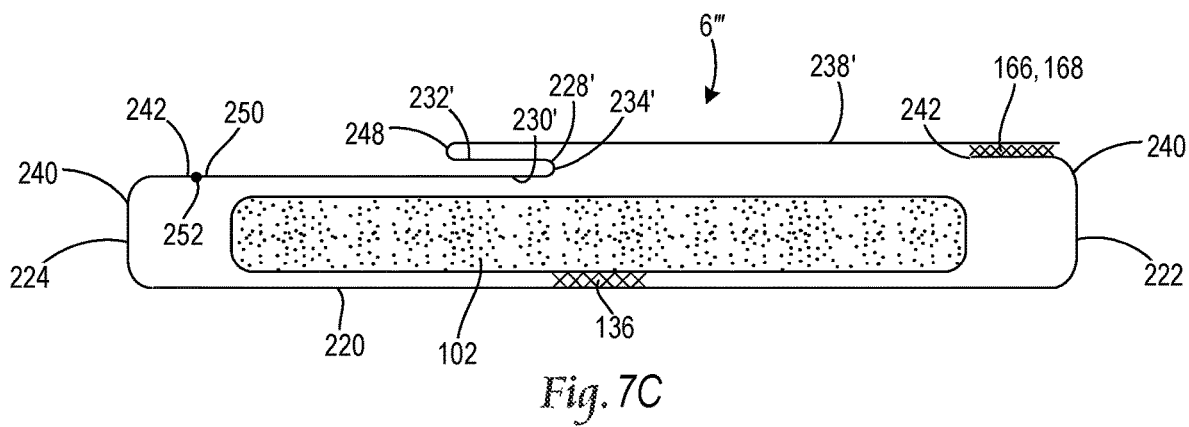
FIGS. 7C is a cross-section of an expansion loop according to another embodiment of the invention.

As further illustrated in FIG. 7C, an expansion loop 6''' according to another embodiment is described. The side wall end 242 of the first side wall 222 is coupled to the second side 238' at a second side end 250 to form a second side bond 252, which may be provided by an adhesive 166 or ultrasonic bonding 168 or another known method of bonding.

Figure 7D:
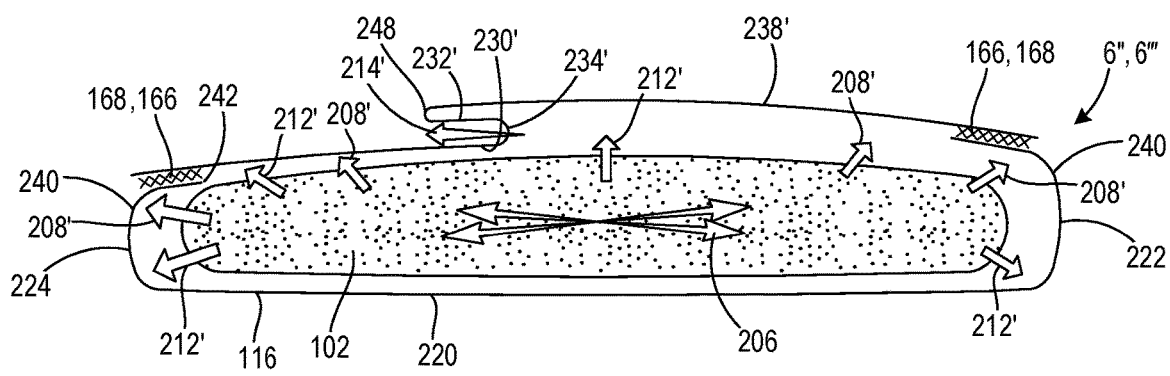
FIG. 7D illustrates operation of the expansion loop of FIG. 7B according to an embodiment of the invention.

As further illustrated in FIG. 7D, a method of operation of the expansion loop 6" of FIG. 7B and the expansion loop 6''' of FIG. 7C is described. The core 102 experiences an expansion 206, causing the core 102 to press 208' against the expansion loop material 116 surrounding the core 102. The press 208' of the core 102 causes the trough base 234' and the second elbow 248 to travel 214' toward one another.

Figure 8A:
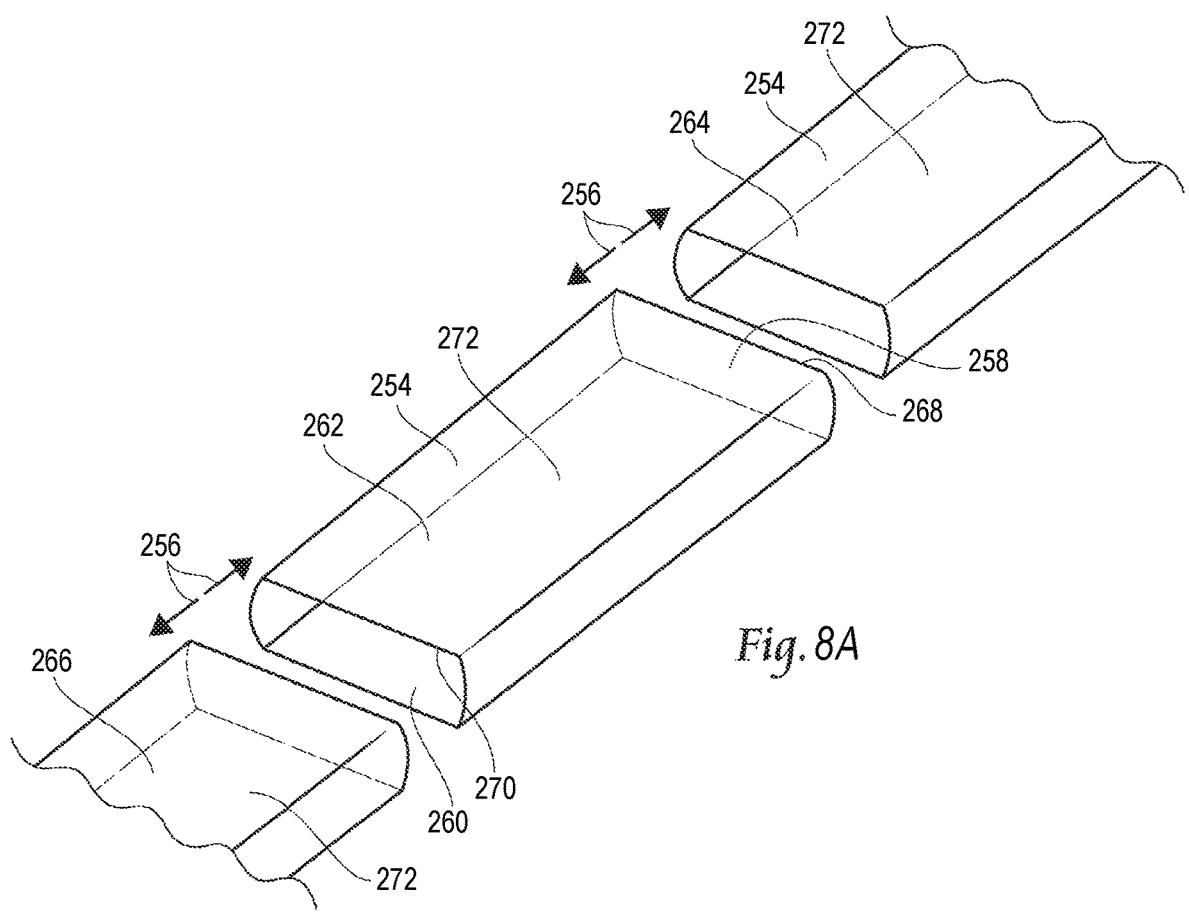
FIGS. 8A-D illustrate a method of manufacturing a case assembly according to an embodiment of the invention.
Figure 8B:
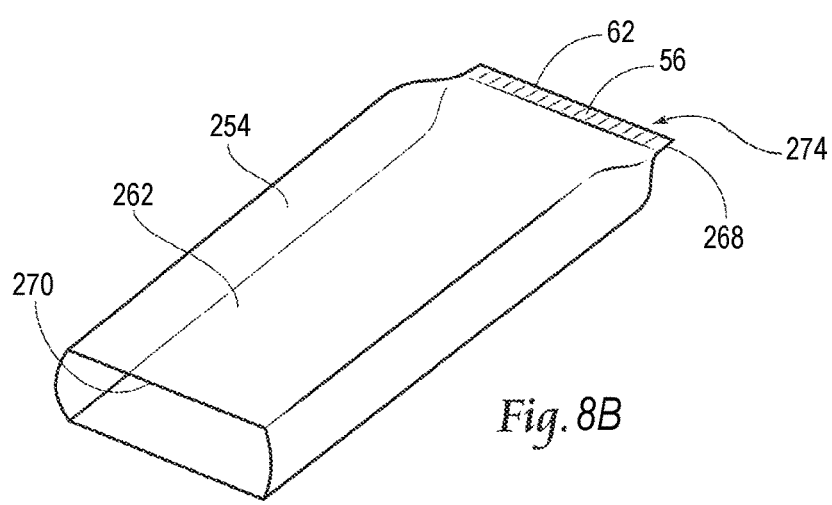
Figure 8C:
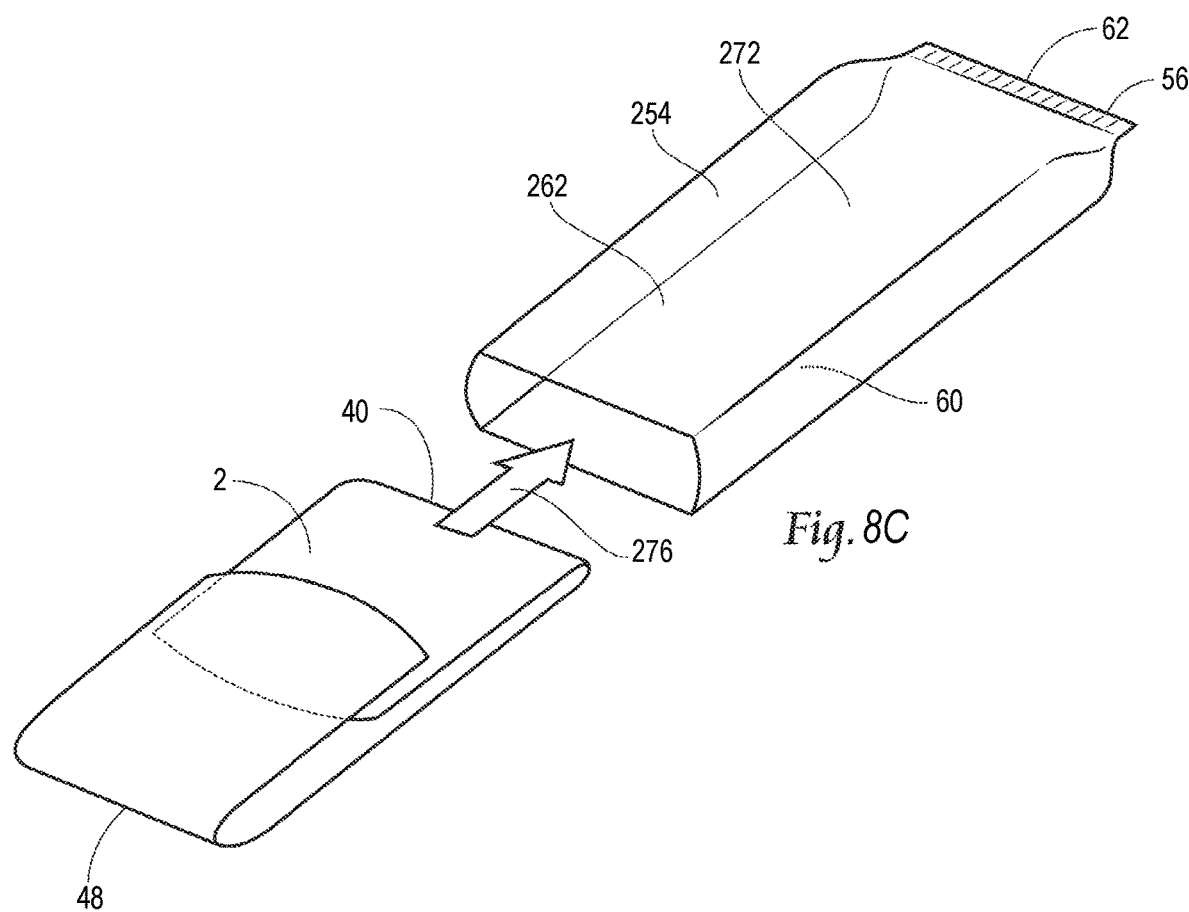
Figure 8D:
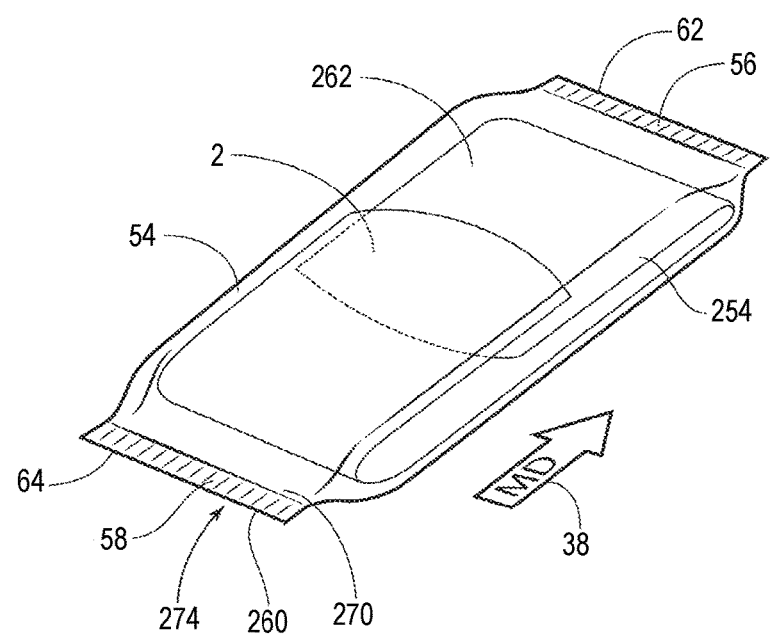

Referring to FIGS. 8A-8D, a method for manufacturing the package assembly 36 of FIG. 2 is described. The method as described in FIGS. 8A-8D provides for the application of the embodiments of the expansion loop (6, 6', 6", 6''') as described in this application. As illustrated in FIG. 8A, a case material 254 comprising a tubular orientation is cut (step 256) at least substantially perpendicular to the machine direction 38 at a first case material location 258 and at a second case material location 260 to create a first tube section 262, a second tube section 264, and a third tube section 266. Each tube section 262, 264, 266 (and subsequent tube sections) has a first tube section end 268 and a second tube section end 270 separated by the tube section body 272. As illustrated in FIG. 8B, sealing (step 274) the first tube section end 268 creates a first seal 56 that provides the case end 62 of the first tube section 262. As illustrated in FIG. 8C, the tube section body 272 of the first tube section 262 includes the first seal 56 and the case cavity 60. The hygiene product 2 is inserted (step 276) into the second embodiment case cavity 60 such that the first fold 40 is close to the first second embodiment case end 62 and the first seal 56. As illustrated in FIG. 8D, the case material 254 of the second tube section end 270 is sealed 274 to create the second seal 58 and the second embodiment case end 64.

Beneficially, embodiments of the invention thus provide a hygiene product and method of manufacturing thereof that allows a liquid absorbent core of the product to unfold the material enclosed therearound to avoid breaking or damaging the enclosing material. An expansion loop of material provided in the enclosing material allows the space enclosed by the material to grow with expansion of the core without stretching the material. Use of the hygiene product provides for a greater quantity of liquid to be retained and stored by an absorbent core material due to an increased expansion space.

Therefore, according to one embodiment of the invention, an expandable absorbent structure comprises an expansion loop core configured to expand in response to absorption of a liquid and an expansion loop material structure surrounding the expansion loop core and having a trough therein, wherein the trough is formed from a first portion of the expansion loop material structure folded over a second portion of the expansion loop material structure at a first elbow of the expansion loop material structure. In response to an increase in size of the expansion loop core, the expansion loop core presses against the expansion loop material structure to cause a length of the trough to decrease.

In accordance with another embodiment of the invention, an absorbent product comprises a first core and an expansion loop positioned adjacently to the first core. The expansion loop comprises a second core configured to expand in response to absorption of a liquid and a loop material surrounding the second core. The loop material comprises a first portion, a second portion overlapping the first portion, and a first elbow joining the first portion to the second portion. The first portion, the second portion, and the first elbow form a trough. The first core and the second core expand in response to liquid absorption. In response to expansion of the second core, the second core presses against the loop material to reduce a length of the trough.

In accordance with another embodiment of the invention, a method of making an expandable absorbent structure comprises positioning a liquid absorption core adjacently to a liquid permeable material and folding a first leg of the liquid permeable material about a first end of the liquid absorption core to create a trough in the first leg. The trough is formed by a first portion of the first leg, a second portion of the first leg overlapping the first portion, and an elbow of the first leg joining the first portion to the second portion. The method also comprises folding a second leg of the liquid permeable material about a second end of the liquid absorption core, the second end of the liquid absorption core opposite the first end of the liquid absorption core. The method also comprises bonding the first leg to the second leg.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description but is only limited by the scope of the appended claims.

What is claimed is:

1. An expandable absorbent structure comprising:
   an expansion loop core configured to expand in response to absorption of a liquid;
   an expansion loop material structure directly surrounding the expansion loop core and having a trough therein, wherein the trough is formed from a first portion of the expansion loop material structure folded over a second portion of the expansion loop material structure at a first elbow of the expansion loop material structure, and wherein the expansion loop material structure has a first leg joined to a second leg; and
   a bond formed between the first leg and the second leg in close proximity to an end of the first leg and an end of the second leg;
   wherein, in response to an increase in size of the expansion loop core, the expansion loop core presses against the expansion loop material structure to cause a length of the trough to decrease.

2. The absorbent structure of claim 1, wherein the expansion loop material structure comprises:
   a first side wall;
   a second side wall; and
   a middle section between the first and second side walls; and
   wherein the first elbow of the expansion loop material structure is positioned closer to the middle section than to the first and second side walls.

3. The absorbent structure of claim 1, wherein the expansion loop material structure comprises a continuous sheet of material; and
   wherein the second leg comprises the first and second portions of the expansion loop material structure folded over each other.

4. The absorbent structure of claim 1, wherein the trough is formed in the first sheet of material adjacently to the first leg end of the first sheet of material.

5. The absorbent structure of claim 4, wherein a second trough is formed adjacently to the second leg end of the first sheet of material;
   wherein the second trough is formed from a third portion of the expansion loop material structure folded over a fourth portion of the expansion loop material structure at a second elbow of the expansion loop material structure; and
   wherein the third and fourth portions are adjacent to the second leg end of the first sheet of material.

6. The absorbent structure of claim 1, wherein the trough is formed between the first and second leg ends of the second sheet of material.

7. The absorbent structure of claim 6, wherein the first elbow of the expansion loop material structure is positioned closer to a middle section of the expansion loop core than to the first and second leg ends of the second sheet of material.

8. The absorbent structure of claim 6, wherein the expansion loop material structure has a third portion folded over the second portion of the expansion loop material structure at a second elbow adjacent to the trough.

9. The absorbent structure of claim 1, wherein the expansion loop core comprises at least one of a fibrous material and a super absorbent polymer.

10. An absorbent product comprising:
    a first core; and
    an expansion loop positioned adjacently to the first core and comprising:
    a second core configured to expand in response to absorption of a liquid; and
    a loop material directly surrounding the second core and comprising:
       a first portion;
       a second portion overlapping the first portion, wherein the loop material has a first leg joined to a second leg;
       a bond formed between the first leg and the second leg in close proximity to an end of the first leg and an end of the second leg; and
       a first elbow joining the first portion to the second portion;
    wherein the first portion, the second portion, and the first elbow form a trough;
    wherein the first core and the second core expand in response to liquid absorption; and
    wherein, in response to expansion of the second core, the second core presses against the loop material to cause a length of the trough to decrease.

11. The absorbent product of claim 10, wherein the expansion loop is configured to absorb liquid transferred thereto via the first core.

12. The absorbent product of claim 10 further comprising:
    a liquid permeable layer;
    a liquid impermeable layer coupled to the liquid permeable layer; and
    wherein the first core and the expansion loop are positioned between the liquid permeable layer and the liquid impermeable layer.

13. The absorbent product of claim 12 further comprising an acquisition distribution layer positioned between the first core and the liquid permeable layer.

* * * * *